(12) United States Patent
Jacobsen et al.

(10) Patent No.: US 6,763,720 B1
(45) Date of Patent: Jul. 20, 2004

(54) MEASURING SYSTEM INCLUDING POSITIONING AND DATA TRANSFER

(75) Inventors: Jostein Jacobsen, Lommedalen (NO); Odd Torset, Jar (NO); Øyvind Lund-Johansen, Vettre (NO); Knut T. Skaar, Oslo (NO); Magne Ivar Steinset, Irondheim (NO); Arild Søraunet, Stjørdal (NO)

(73) Assignee: Det Norske Veritas AS, Veritasveien (NO)

( * ) Notice: Subject to any disclaimer, the term of this patent is extended or adjusted under 35 U.S.C. 154(b) by 0 days.

(21) Appl. No.: 09/979,387

(22) PCT Filed: May 24, 2000

(86) PCT No.: PCT/NO00/00170

§ 371 (c)(1),
(2), (4) Date: Nov. 20, 2001

(87) PCT Pub. No.: WO00/73739

PCT Pub. Date: Dec. 7, 2000

(30) Foreign Application Priority Data

May 27, 1999 (NO) .............................................. 992558

(51) Int. Cl.[7] ............................................. G01N 29/10
(52) U.S. Cl. ....................................................... 73/602
(58) Field of Search .......................... 73/597, 599, 579, 73/602

(56) References Cited

U.S. PATENT DOCUMENTS

| | | | | |
|---|---|---|---|---|
| 2,538,114 A | * | 1/1951 | Mason ........................ | 73/630 |
| 3,732,947 A | * | 5/1973 | Morah et al. ................. | 367/35 |
| 3,741,334 A | * | 6/1973 | Kaule .......................... | 73/630 |
| 3,798,961 A | | 3/1974 | Flambard et al. ............. | 73/644 |
| 3,844,166 A | | 10/1974 | Carossi et al. ............... | 73/622 |
| 3,914,987 A | * | 10/1975 | Bickel et al. ................. | 73/609 |
| 4,033,178 A | | 7/1977 | Holt et al. .................... | 73/644 |
| 4,255,798 A | * | 3/1981 | Havira ......................... | 367/35 |
| 4,912,683 A | | 3/1990 | Katahara et al. ............. | 367/25 |
| 5,047,990 A | | 9/1991 | Gafos et al. ................... | 367/6 |
| 5,303,207 A | | 4/1994 | Brady et al. ................ | 367/134 |
| 5,440,929 A | | 8/1995 | Huang et al. ................. | 73/628 |
| 5,469,744 A | | 11/1995 | Patton et al. ................. | 73/644 |
| 5,557,970 A | | 9/1996 | Abbate et al. ................ | 73/597 |
| 5,942,687 A | * | 8/1999 | Simmonds et al. ........... | 73/579 |
| 6,057,927 A | * | 5/2000 | Levesque et al. ........... | 356/432 |
| 6,397,680 B1 | * | 6/2002 | Levesque et al. ............. | 73/602 |

FOREIGN PATENT DOCUMENTS

| | | |
|---|---|---|
| EP | 0 060 952 A2 | 9/1982 |
| EP | 0 267 840 B1 | 9/1991 |
| NO | 179926 B | 9/1996 |
| WO | WO 99/31499 | 6/1999 |

OTHER PUBLICATIONS

International Search Report for PCT/NO00/00170 dated Sep. 7, 2000 (WO 00/73739 A1).
Internatioanl Preliminary Examination Report for PCT/NO00/00170 dated Sep. 27, 2001.
Written Opinion for PCT/NO00/00170 dated Jul. 10, 2001.

* cited by examiner

Primary Examiner—Hezron Williams
Assistant Examiner—Rose M. Miller
(74) Attorney, Agent, or Firm—Abelman, Frayne & Schwab

(57) ABSTRACT

The invention provides a system for measuring, characterizing, verifying and position-determining material properties of a selected object to be measured, in particular thickness distribution. A mobile measuring unit which is manouvered and operated manually or with the aid of a remote-control transport device senses half-wave resonance in objects to be measured and computes the thickness distribution. A new, accurate, partly acoustic positioning system determines the position of the measured area.

19 Claims, 8 Drawing Sheets

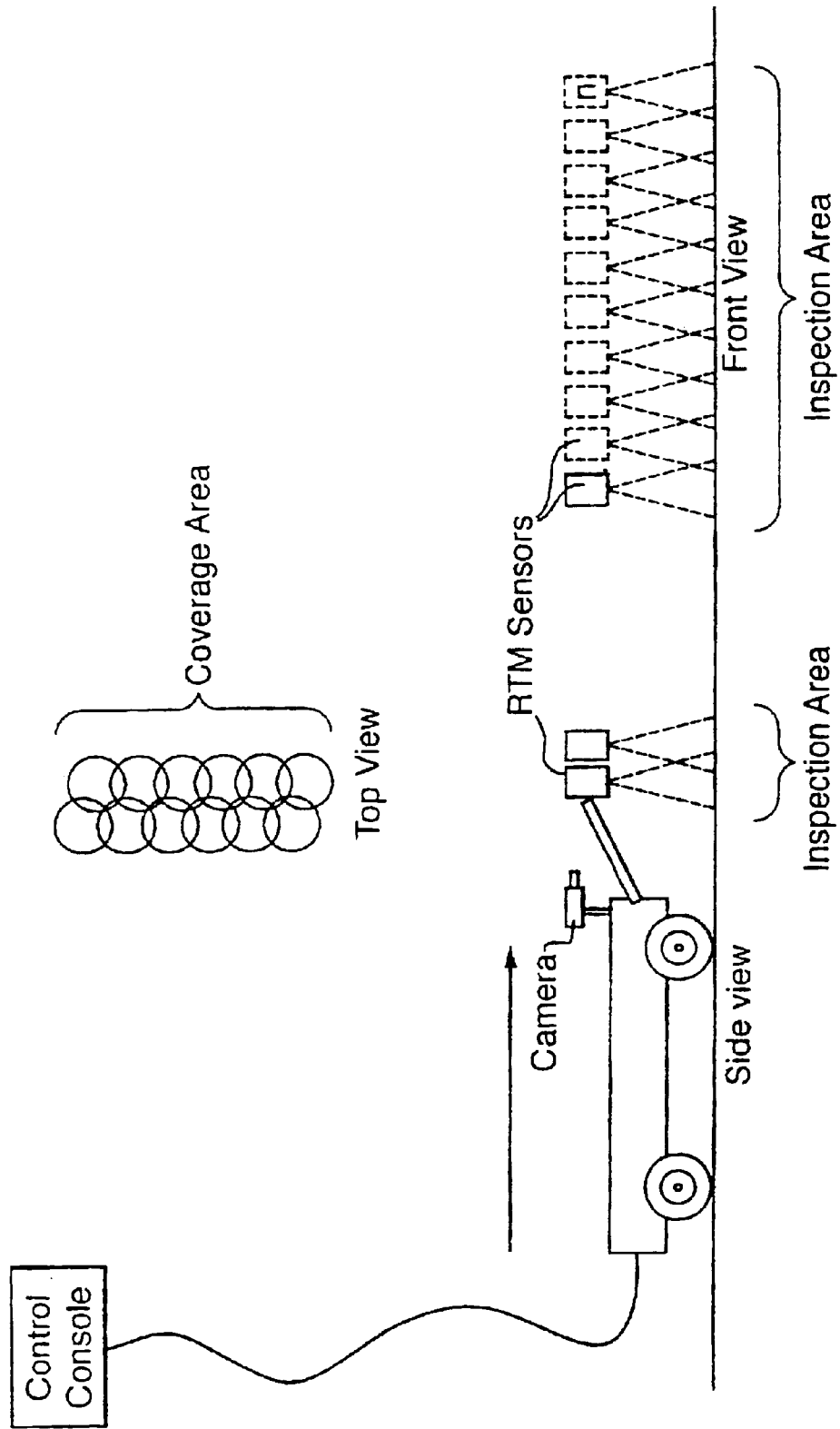

MEASURING SYSTEM INCLUDING POSITIONING AND DATA TRANSFER

The invention relates to a system for measuring thickness of material, and more specifically it relates primarily to a method and a sensor for measuring thickness distribution in a material by half-wave resonance in the material that is subjected to measurement. Furthermore, the invention relates to an automatic positioning system suitable for positioning one or more sensors in a system for measuring distribution of thickness in material in an object that is to be measured.

A number of materials used in pipelines, ship hulls, tanks and other structures are of such a nature that they may disintegrate or change with time as a consequence of corrosion, mechanical wear and so forth. This disintegration or change may result in the weakening of the supporting structural materials due to some of the material being discharged into the surrounding environment, or because materials alter their characteristic properties so that they no longer fulfil their desired aims. The effect of these processes of disintegration and change is often a reduction in the amount of the effective material. In structures of sheet material this may have the effect of reducing the sheet thickness. It is frequently found that the reduction of the material resulting from the aforementioned causes is not evenly distributed, but that at times there are large variations in thickness over relatively small areas, such as, for example, can be observed when a protective coating of paint on steel plate has been damaged in such a way that there is direct moisture contact with the steel, and where corrosion pitting has been allowed to develop. Similar corrosive attack can also be observed, e.g., on ship hulls. Since the actual hull is usually a part of the supporting structure of a ship, and since by being impenetrable to liquid it ensures both the ship's buoyancy and that the ship's load is not discharged into the surrounding environment, it is essential to be keep track of the state of the material at all times and to chart any disintegration of the structural material which may cause a weakening of the structure. Similar needs for monitoring and charting the state of material exist in a number of other areas in addition to that described above for ship hulls, such as bridge and building structures, pipes, boilers and tanks in industrial plants, road and rail vehicles.

Over the years, a number of different methods have been employed for measuring thickness of material, and among the non-destructive methods, measuring methods utilising sound waves have dominated in recent decades. In a common form, ultrasound is used for measurements according to the echo principle, where thickness of material is determined on the basis of time-of-flight measurements for a short ultrasonic signal, often at a single frequency, which is reflected from junctions between materials of different quality. A thickness measurement is thus made by registering the differences in time-of-flight between the ultrasonic signals returned by reflection, and from the registered differences in time-of-flight, thicknesses are calculated on the basis of knowledge of the speed of sound in the materials through which both the transmitted and reflected ultrasonic signals propagate. When measuring thickness using ultrasound according to the echo principle, the ultrasonic signal is transmitted from a measuring head in the form of a beam having a small cross-section and a relatively small angular aperture. The advantage of using a beam having a small cross-section and small angular aperture is that it reduces the probability of the measuring accuracy being impaired because the beam covers an area including material of varying thickness. However, this means that the area which is characterised is correspondingly small, and that the number of measurements necessary to cover a particular area thus increases correspondingly. In practice this means that such measurements on large structures are carried out at relatively long intervals because the total measuring period would otherwise be unacceptable. Consequently, when making such point-by-point measurements there will be large areas which in actual fact are not examined, and where it is conceivable that there might be unacceptable deviations from the desired thickness of material which will thus remain undiscovered by such a method.

Norwegian Patent Publication No. 179926 in the name of Red Band makes known a method for automatic status check, inspection, cleaning and/or surface treatment of structures, especially measurement of thickness of steel plate structures and pipes using ultrasonic signals from a remote-controlled, self-propelling unit. The self-propelling unit is moved continuously around the test area, and a transmitter transmits an ultrasonic signal in a direction substantially perpendicular to the surface of the structure. A reflected signal is received by a receiver, and thickness and material quality at the test point in question are determined on the basis of this signal, together with parameters such as time-of-flight for the reflected signal and material constants. The self-propelling unit effects its own positioning with the aid of known points in the structure. All data received about the wave form of the reflected signal is stored in a computer, and thickness and material quality are verified by comparing data for the received signal at one point with data for received signals at neighbouring points. The step is repeated to record data for new test points.

Another method for measuring thickness by means of sound waves is described, in for example, U.S. Pat. No. 3,844,166, wherein with the aid of registration of half-wave resonance in the object which is subjected to measurement it is possible to determine thickness of material in a rather limited area. The patent discloses a method and a device for measuring thickness, wherein ultrasound is used which is frequency-modulated in accordance with a sinusoidal law. The sound waves are emitted from a transducer which focuses the wave in towards a point at which the thickness of material is to be measured. Sound waves which are emitted from the object are received by a receiver means designed for the purpose. At frequencies where half-wave resonance occurs, a registration is made of the time it takes to count two predetermined numbers of whole periods of the acoustic signal, and the registered time then forms a part of a specified calculation formula whereby the thickness of material at the selected test point is determined. As for the previously described measuring method, this last-mentioned method also gives a single value for the thickness of material at one point as a result of each individual measurement.

Patent Application No. 153029, laid open by the Norwegian Patent Office, makes known an inspection apparatus for ultrasonic investigations of the wall of a pipe whilst the apparatus is moved along the interior surface of the pipe. The apparatus comprises at least one sensor in the form of a wheel probe wherein at least one ultrasonic transducer is located in a chamber filled with acoustic couplant, wherein the chamber is in the form of a rotatable wheel having a compact elastic tyre positioned adjoiningly over a rigid annular rim. The transducer is secured inside the wheel relative to the body of the inspection apparatus in a position where the emitted signal at all times is directed towards the point at which the wheel is in contact with the material that is being inspected, whilst the wheel turns as the apparatus moves along the surface of the material. The acoustic signal is coupled via the couplant, through the annular rim and then via the compact elastic tyre which is in contact with the surface of the material of the pipe that is to be inspected. The sensor is also provided with one or more elastic membranes which, for pressure equalising purposes, merely serve to take up any variations in volume which may occur in the couplant or in possible gas present in the wheel-shaped sensor chamber owing to temperature variations and partly owing to pressure variations when, for example, being raised or lowered. This measuring apparatus is thus limited, at each measuring sequence, to investigate only a very limited area of the material which is under the tangential points between the material surface and the wheel probe.

It is therefore desirable to have available a method and an apparatus which allow data to be obtained on each individual measurement over a large continuous area which characterises completely any varying thickness of material over the whole area. In cases where charting thicknesses of material comprises areas which have an extent greater than the area that can be covered by a measuring apparatus according to the invention, it is necessary to make a controlled number of measurements until the whole of the area in question has been covered, and at the same time determine the position of each individually measured area. Possibilities for controlling the measurements will also be of importance for measurements of known objects to be measured, as repetition of measurements during, e.g., periodic inspections, could be rendered considerably more efficient by concentrating the measuring activity in particular areas where earlier measurements have revealed substantial occurrences of changes in the material. Control of measurements on the basis of knowledge of the structure of the object to be measured will also be desirable in order to be able to make a more correct interpretation of the measuring results.

The present invention provides a new apparatus and a new method whereby it is possible to make an all-over measurement of the thickness distribution in the material of an object that is to be measured over a chosen continuous area of the said object.

Furthermore, the invention provides a new automatic positioning system for rapid and accurate position determination, which is suitable for determining the position of areas of an object which are subjected to thickness distribution measurements. A new measuring system is also provided which in addition to said new measuring apparatus and said new positioning system may also include one or more transport apparatuses and data transfer and processing systems, with which measuring system it is possible to make controlled measurements of thickness distribution in a material of a known object to be measured, and to collect, store and present the measuring results.

The invention will now be explained in more detail with the aid of exemplary embodiments with reference to the attached drawings, wherein:

FIG. 9 shows a possible embodiment of a measuring system with a plurality of sensors, operated by means of a remote-control transport unit, for thickness distribution measurements according to the invention.

The present invention provides a measuring system as shown in FIG. I for measuring and storing position-determined data concerning distribution of thickness of material over chosen continuous areas composed of one or more smaller test areas, characterised in that it includes:

1) mobile apparatuses for all-over measurement of thickness distribution in the material of the object to be measured, which apparatuses, by using broadband acoustic sensors adapted for the purpose and having relatively large surface cover measure and compute the thickness distribution in the material beneath the sensors by analysing the half-wave resonance energy content in acoustic signals which are emitted from the object subjected to measurement in response to broadband acoustic signals which are transmitted into the said object, the aforementioned signals being received and transmitted respectively by the aforementioned broadband acoustic sensors;

2) an automatic, three-dimensional positioning system, which positioning system by measuring differences in time-of-flight between temporally related electromagnetic and acoustic positioning signals emitted from respectively reference stations located at predetermined positions and mobile units associated with the aforementioned acoustic sensor, using intermediate base stations which receive the electromagnetic and acoustic positioning signals, computes the positions of mobile units without requiring line-of-sight between reference stations and mobile units;

3) a data collecting unit for collecting and processing at least the thickness distribution data provided by the aforementioned apparatuses for measuring thickness distribution and the three-dimensional position data of the test points provided by the aforementioned positioning system;

4) a data transfer unit for transferring to the aforementioned data collecting unit at least the thickness distribution data from the aforementioned apparatuses for measuring thickness distribution and the three-dimensional position data of the test points from the aforementioned positioning system;

5) a database containing data relating to the object subjected to measurement for at least application when carrying out thickness distribution measurements and positioning, which database is capable of being updated with new data from the aforementioned data collecting unit.

Figure 1:
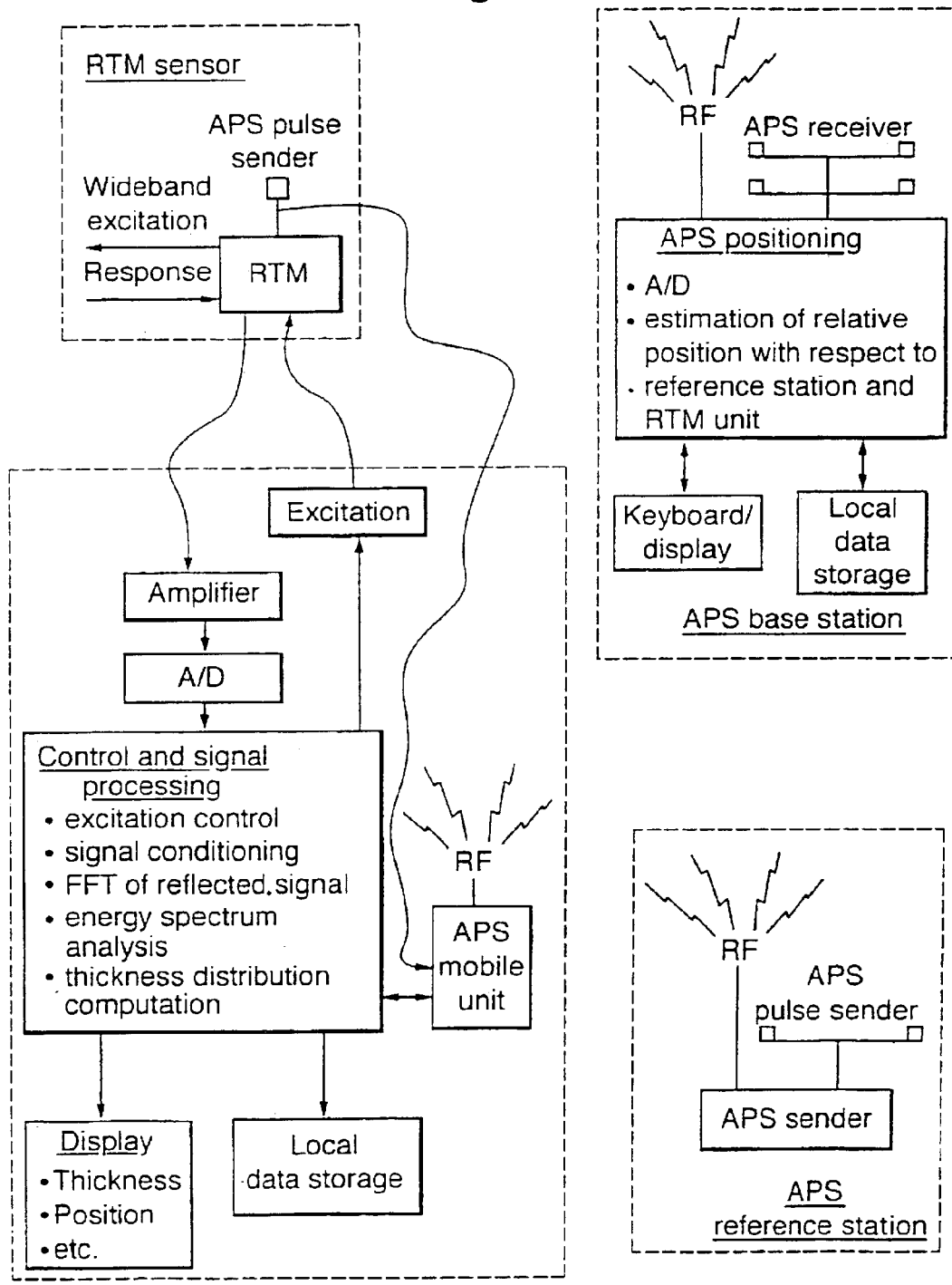
FIG. 1 is a block diagram of a possible embodiment of a system for measuring thickness distribution in a material including positioning according to the invention.
Figure 2:
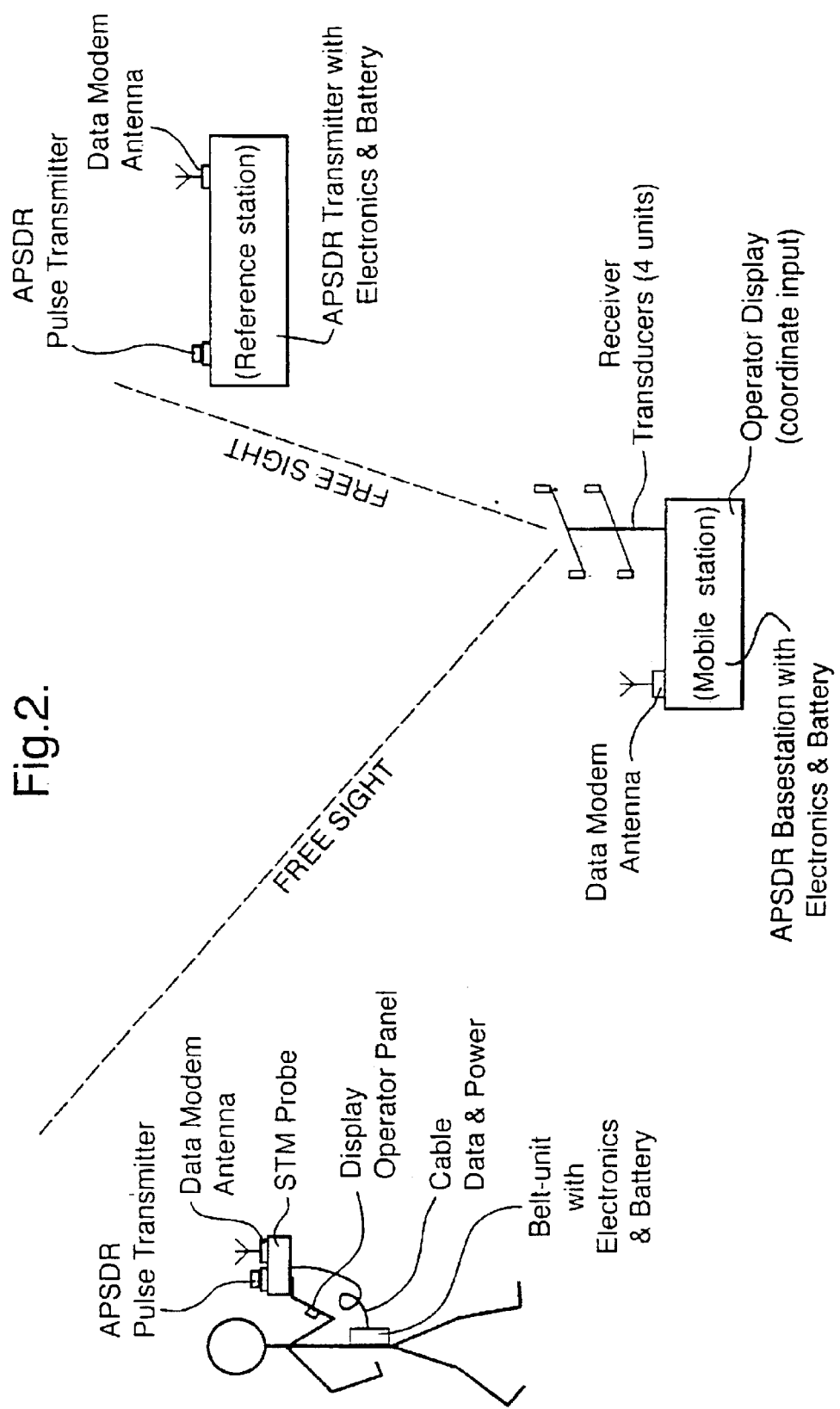
FIG. 2 shows a possible embodiment of a manually operated system for measuring thickness distribution in a material according to the invention.
Figure 3:
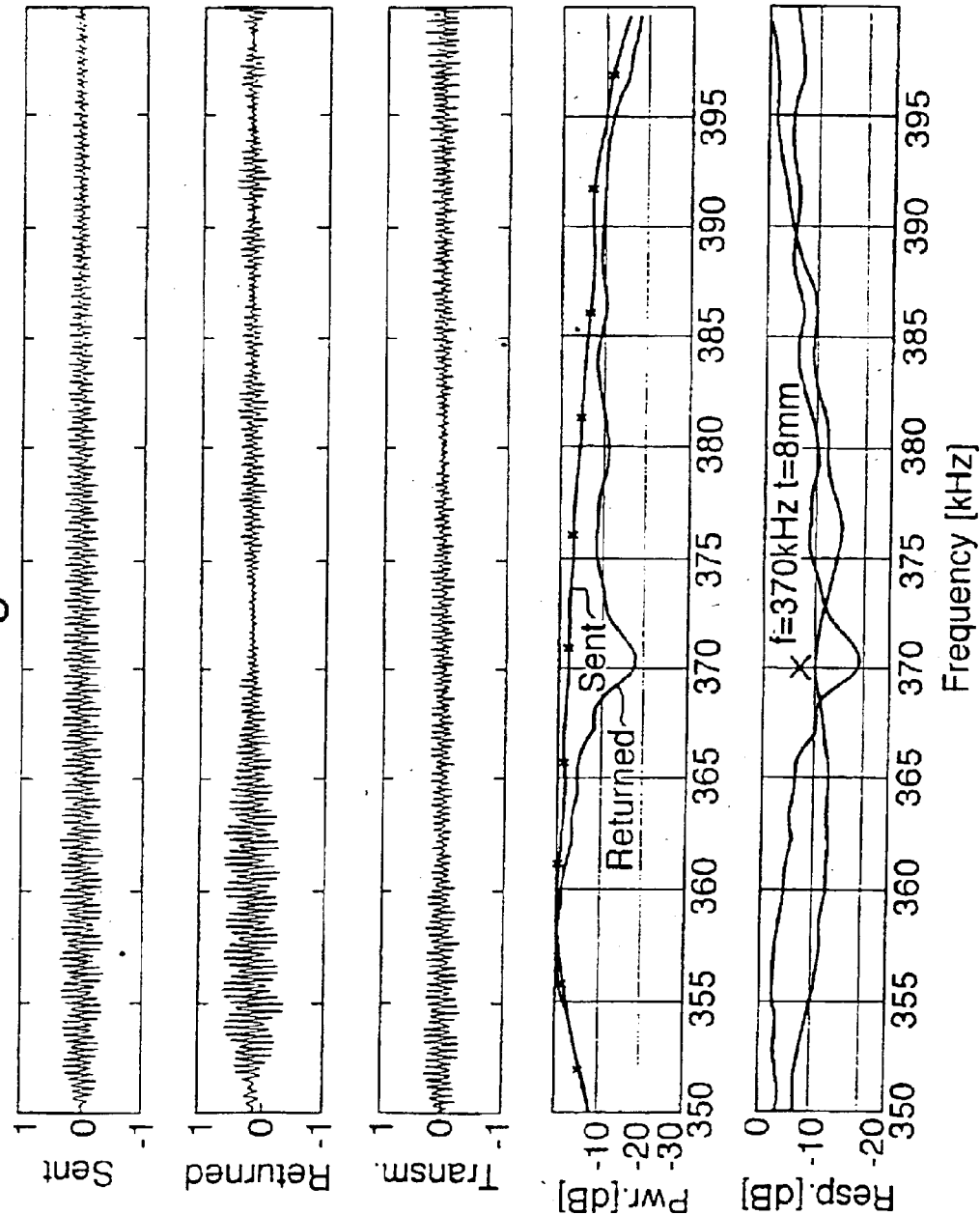
FIG. 3 shows examples of signal sequences during a thickness distribution measurement according to the invention.
Figure 4:
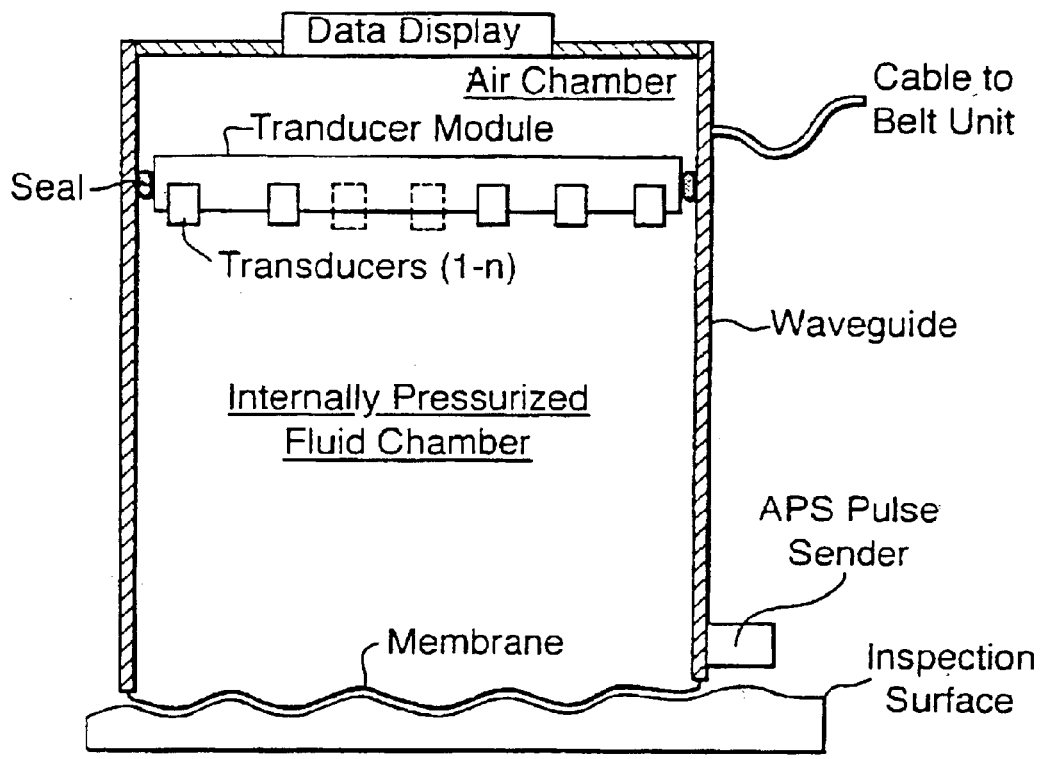
FIG. 4 shows in section schematically a drawing of a possible measuring sensor according to the invention.

In FIG. 1 there is a schematic illustration of a portable embodiment of the invention wherein a handheld sensor for thickness distribution measurements is equipped with a positioning transducer and RF antenna, wherein these in turn are connected to a power supply and electronic unit which the operator carries in his belt. FIG. 2 illustrates a similar system and indicates a possible need for line-of-sight between individual units in the system. For control of the measurements, the measuring system may also include a control unit connected to the database, wherein the control unit produces control data for controlling thickness distribution measurements. The control information is transmitted to the operator who then, with the aid of the positioning system, places the measuring sensor in the correct position in order subsequently to make a specific measurement of the given area For measurements of large objects such as, for example, the hull of a ship which is in the water, it would be advantageous to replace manual operation which could have been carried out by, for example, a diver with a controllable submarine vessel as shown in FIG. 4. The measuring system according to the invention will then also include a mobile, controllable propulsion unit which receives the control data and which serves as a propulsion unit to move the measuring sensors across the object that is to be measured in order to carry out thickness distribution measurements in accordance with the control data it receives.

FIG. 9 shows a system having a controlled propulsion unit which moves a plurality of sensors for thickness distribution measurements which both efficiently and relatively quickly can provide complete coverage of a large test area The illustrated array indicates a possible embodiment with two rows of sensors, wherein the rows are offset approximately half a sensor width relative to one another to give a certain degree of overlapping. A vessel or propulsion unit which forms a part of the measuring system according to the invention can also be controlled using a television camera which by transmitting pictures to an operator console or panel will allow a remote operator to monitor the progress and take corrective measures if necessary. Via an operator console, there is also the possibility of controlling the measurements manually.

Sensor arrays in other patterns and embodiments will also be suitable for measurements of objects having a varying degree of surface curvature, in particular with a view to measuring elongate, cylindrical objects such as, for example, circular-cylindrical pipes, where sensors placed on the periphery of a circle or an extended helix will allow continuous measurements of such objects. Such sensor arrays may conceivably be moved through a pipeline or the like by means of a wirepull, a self-propelling transport device, by means of the pressure/current of a fluid or in another manner.

The present invention also provides a method for all-over measurement of the thickness distribution in the material of an object to be measured over chosen continuous areas, characterised in that it includes:

1) generating broadband electrical excitation signals which include frequency components within the test area in question;
2) converting aforementioned broadband electrical excitation signals into broadband acoustic signals;
3) transmitting the aforementioned broadband acoustic signals into the object to be measured;
4) receiving acoustic response signals emitted from the object to be measured in response to the aforementioned transmitted broadband acoustic signals;
5) converting the aforementioned acoustic response signals emitted by the said object into electrical receiver signals;
6) conditioning the aforementioned receiver signals;
7) analysing said conditioned receiver signals to derive spectral distribution of the signal energy in the aforementioned conditioned receiver signals;
8) computing thickness distribution on the basis of the half-wave resonance content in the aforementioned spectral distribution.

For the storage of the measuring results for subsequent processing or, for example, for planning and carrying out later similar investigations, the method could also include registration of the results of the thickness distribution computations. Furthermore, it may be appropriate for an operator or inspector to be given an immediate presentation of the measuring results in order to, for example, either monitor the quality of the results or to decide at once any measures required in consequence of the results obtained, and the method could therefore also include a step for the presentation of the results with associated processing for presentation in a manner suitable therefor. The generation of broadband excitation signals may be done with the aid of an electronic signal generator which can be set for an suitable signal form and signal strength, preferably by means of a control unit which monitors the reflected signal. A suitable excitation signal can be characterised as follows:

the excitation signal is split up into a number of separate excitation pulses:

each individual excitation pulse may have any form that has a frequency content which covers the entire frequency range in question;

examples of pulse forms include sin(x)/x, chirp, transient and white noise;

the duration of each individual excitation pulse is adjusted so that it does not interfere with the reflected signal (response) from the object subjected to measurement;

the time interval between each excitation pulse has been adapted so that reflected pulse from the structure has fallen below a given level;

the power content in each individual pulse is adjusted, preferably automatically, within given limits until the power in the reflected signal has reached a desired level;

the characteristic parameters for the pulse are controlled by software in the control unit.

A typical reflected signal that is received and processed by the method according to the invention can be characterised as follows:

the signal consists of two main parts, a reflection and a <<tail>>;

the primary reflection comes first and contains mainly frequencies which do not reflect the half-wave resonance in the object that is to be measured;

the <<tail>> contains mainly frequencies which do reflect the half-wave resonance(s) in the object that is to be measured;

both primary reflection and the <<tail>> can be used in computing thickness and thickness distribution;

the software which controls the analysis and computation determines, on the basis of given criteria, which parts of the reflected signal and <<tail>> are to be given importance in the computation of mean thickness and thickness distribution of the object that is to be measured;

the power content of the part of the reflected signal which it is desirable to use for the thickness computation is adapted to the measuring range of the AD converters by controlling emitted power and/or adjusting the amplification of the received, reflected signal;

the method carries out adjustment of the power content of the reflected signal by automatic control through the software (autoranging).

The signal processing and the thickness distribution computation made by means of the method according to the invention may include the following:

- FTT (Fast Fourier Transform) is taken of the part of the reflected signal that it is desirable to use in the thickness computation;
- based on FFT, an energy spectrum is formed which reflects the energy content in the reflected signal as a function of frequency;
- the energy spectra from a number of pulses are averaged to give a better estimate of the dynamic properties of the object to be measured;
- the energy spectrum is normalised on the total frequency characteristic of the sensor;
- based on static estimates of the normalised energy spectrum, the mean frequency (fm), lower frequency (fn) and upper frequency (fØ) are found;
- based on these characteristic frequencies and the sound velocity in the object that is to be measured, the characteristic thicknesses of the object are found;
- the method finds mean thickness and thickness distribution of the object that is to be measured at the area in questions by means of energy considerations $$T_{MEAN} \approx E = \int_{f_1}^{f_2} \int^A g(f)\, dA\, df$$

- the phase in the response signal is optionally analysed in conjunction with energy considerations, or alone, to further enhance the measurements.

The invention also provides an apparatus for carrying out all-over measurement of thickness distribution in the material of an object to be measured over a chosen continuous area, characterised in that it comprises:

1) a signal generator for generating broadband, electrical excitation signals;
2) a broadband sensor having at least one transducer for converting electrical excitation signals into acoustic excitation signals, transmitting acoustic excitation signals, receiving acoustic response signals and converting acoustic response signals into electrical receiver signals;
3) a processing means for conditioning and spectral analysis of electrical receiver signals;
4) a calculating means for calculating distribution of thickness of material on the basis of spectral analysis results;
5) a control means operatively connected to, for the control thereof, said signal source, sensor, processing means and calculating means.

For storing the results from the measurements, the apparatus will also include one or more registration means connected to said control means and calculating means. A number of different devices may conceivably be used for storage of the results, such as magnetic tape recorders, computer diskettes, semi-conductor based mass storage, disc storage, machine readable paper print-outs, punch tapes and the like. To allow observation of the results by, for example, an operator or an inspector, the apparatus will also include one or more data output means connected to the control means and the calculating means for processing and presentation of the computed thickness distribution. The output devices which are suitable for this purpose may, for example, be paper-based printers, display screens having either colour or monochrome reproduction of the cathode-ray type, the plasma type, the liquid crystal (LCD) type or the like.

Excitation transducers and configurations of such which are suitable for the purpose may also be described by the following:

- the transducer elements can either transmit or receive or both transmit and receive;
- if desirable, the choice may be made to transmit on selected elements and receive on other elements;
- the excitation pulse can be transmitted to all the elements simultaneously or only to selected elements;
- the configuration of excitation transducers can be controlled by means of the software in the control means.

Figure 5:
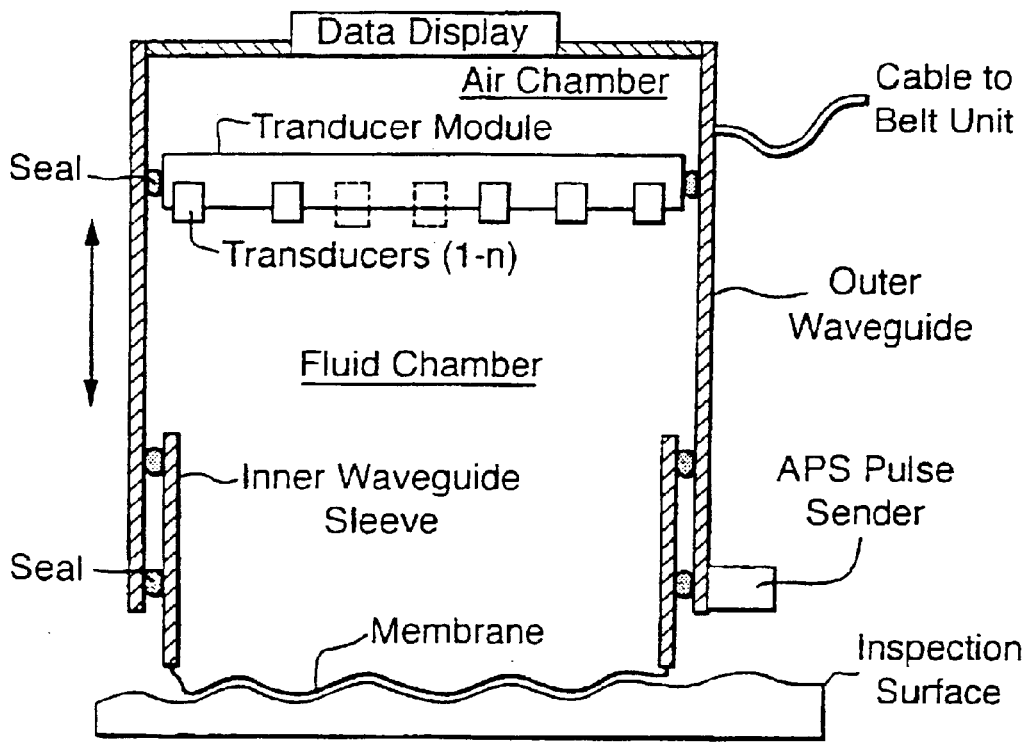
FIG. 5 shows in section schematically a drawing of an alternative possible measuring sensor with pressure control according to the invention.

The invention also provides an acoustic sensor for transmitting and receiving acoustic signals for measuring the thickness of material, characterised in that it includes a transducer assembly having one or more broadband transducers placed in a mounting device, a sensor housing which essentially is filled with a couplant which is suitable for acoustic wave propagation, which sensor housing on one side has a defmed output for acoustic signals, in which sensor housing the aforementioned transducer assembly is placed in an area on the opposite side of the aforementioned output, wherein the aforementioned transducers are so arranged and adapted that acoustic signals emitted from each individual transducer are propagated via the couplant directly to the output of the sensor housing so that the acoustic waves essentially uniformly illuminate the output area. For applications where the object that is to be measured is submerged in a liquid or other fluid which is suitable for the propagation of acoustic waves, such as, for example, fresh water or seawater, it must be ensured that the sensor housing is filled with the liquid or fluid prior to the start of the measuring procedure. In order, inter alia, to simplify sensor maintenance, it will be desirable to have the sensor housing filled at all times with a pure couplant, such as, for example, pure water, a gel, ureol, oil or an almost solid substance, and the sensor housing is then made as a pressure-tight housing and equipped with a more or less flexible or pliable membrane over the output area of the sensor housing to separate the inner couplant of the sensor from the surrounding medium. A pressure-tight sensor configuration equipped with a flexible or pliable membrane, as shown in FIGS. 4, 5, 6 or 7, is suitable for carrying out measurements of objects which are not submerged in a medium which per se produces coupling of acoustic signals. The necessary coupling to a <<dry>> object of this kind is obtained by pressing the output side of the sensor against the object to be measured at suitable pressure so that the surface of the output area is adapted to the surface of the object and is thus well coupled to the object to be measured without the use of a couplant. To ensure good adaptation of the membrane surface to the object to be measured, a sensor filled with a liquid or gelatinous couplant could also be equipped with a pressure pump which controls the pressure of the couplant against the membrane relative to the pressure exerted between the sensor and the object to be measured. One embodiment that is suitable for this purpose is shown in FIG. 5, where the sensor housing is divided so that a first part which includes the output area is arranged so as to be moveable and with sealing in a piston-like manner in relation to the second part of the sensor housing so that the pressure in the interior of the sensor housing is adjusted by the reaction force from the preferably stationary object to be measured when the first part of the sensor housing rests against the said object and the second part of the sensor housing is pressed in the direction of the object. Control of the pressure of the couplant against the membrane can also be obtained in other ways, for example, by means of an additional device which creates pressure in the couplant, such as a controllable pump or pressurised container connected to the sensor housing, which optionally may also interact with a sensor device which senses the pressure exerted by the sensor against the object that is to be measured and thereby adjusts the pressure in the couplant correspondingly. Advantageous embodiments of a sensor according to the invention can also be characterised by the following:

- the sensor may be built up of a plurality of transducer elements which may consist of, e.g., ceramic or piezo films. An example of a transducer is Reson BAS-S, S/N4597002;
- the transducer elements may have the same geometric focus on the object to be measured;
- the transducer elements may be divided into several groups having the same properties (same test area for thickness), so that the groups together cover the entire measuring range of the sensor;
- the transducer elements in each group can radiate the object to be measured from different positions in space;
- the transducer elements can both transmit excitation pulses and register reflected energy;
- the energy can be transmitted between the transducer elements and the object to be measured via a waveguide;
- the transducer elements may have overlapping frequency ranges.

Figure 6:
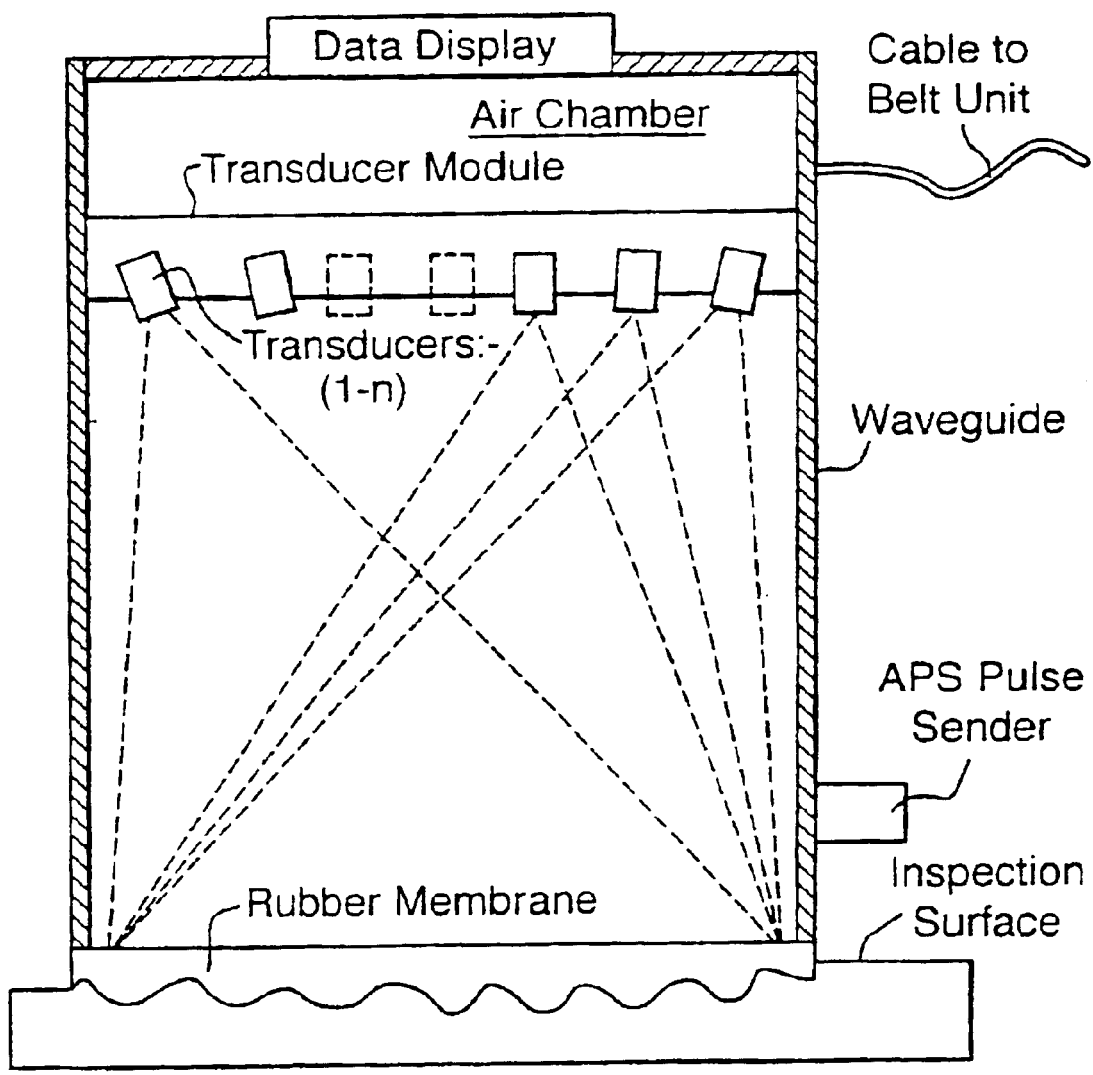
FIG. 6 shows in section schematically a drawing of an alternative possible measuring sensor having a substantially solid couplant and pliable coupling membrane according to the invention wherein also the signal propagation of a broadband acoustic excitation signal in a possible embodiment of a measuring sensor is shown schematically.
Figure 7:
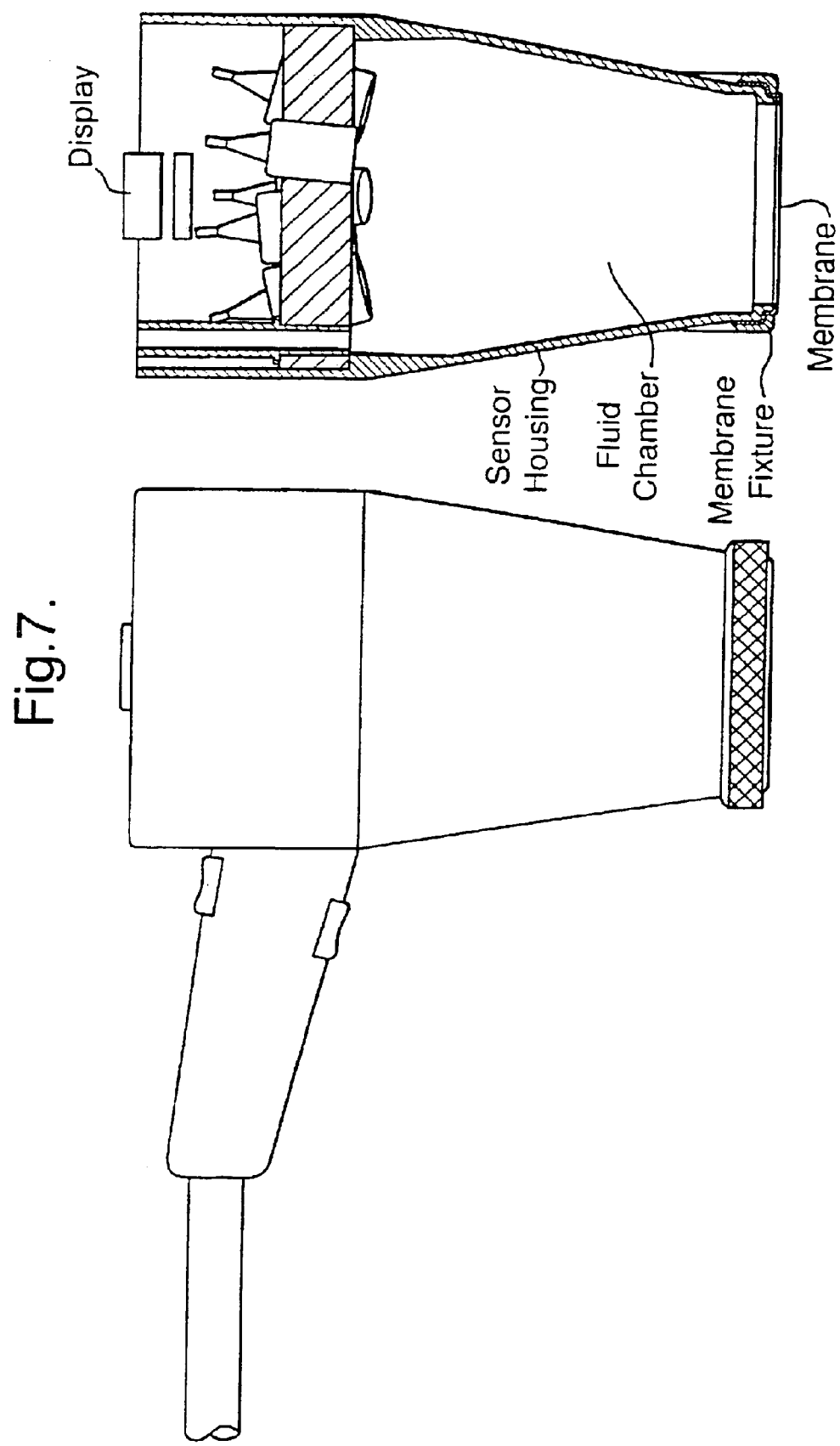
FIG. 7 shows in a possible embodiment a handheld sensor according to the invention.

In a further advantageous embodiment as shows in FIGS. 4, 5 or 6. The transducer assembly is pressure-tight and secured in a pressure-tight manner in the sensor housing so that two chambers are formed in the sensor housing, wherein the first chamber which is defined by the sensor housing, transducer assembly and output essentially will be filled with a medium suitable for acoustic wave propagation, whilst the second chamber is an air chamber which can be used for other purposes, such as, for example, location of electronics, wiring, data display, operating means and the like. When taking measurements of an object which is submerged in a fluid, where the fluid is suitable as a couplant, the membrane in the signal output area can be omitted, and the filling of the first chamber with the fluid as couplant may, for example, take place as the sensor is submerged in the fluid.

The invention also provides a system for automatic three-dimensional positioning in a uniform acoustic signal propagation medium, wherein there is no requirement for line-of-sight between the positioning object and the positioning reference points, characterised in that it includes:

1) at least one reference station unit which includes a control means, at least one receiver for electromagnetic signals, at least one transmitter for electromagnetic signals, and at least one acoustic transmitter, which acoustic transmitter is located in a predetermined first position;
2) at least one mobile unit, which mobile unit includes a control means, at least one receiver for electromagnetic signals, at least one transmitter for electromagnetic signals and at least one acoustic transmitter, which acoustic transmitter is located in a second position;
3) at least one base station unit located in a third position, which base station unit measures and computes its own position and that of the mobile units respectively, which base station includes:
  - at least one control means for at least controlling the transmission of control signals;
  - at least one electromagnetic signal transmitter;
  - at least one electromagnetic signal receiver located on a predetermined location site relative to the aforementioned third position;
  - at least three acoustic receivers wherein respectively each such acoustic receiver is also located at predetermined location sites relative to the aforementioned third position; and
  - a calculating means which is fed position data to indicate the respective first position of the aforementioned reference stations, a control signal from control means, signals from the at least one electromagnetic receiver and at least three acoustic receivers of the respective base station;

wherein the base station electromagnetically transmits control signals and each reference station and mobile unit respectively, in turn and separately, in response to electromagnetically received control signals from the base station transmit at one and the same point of time an electromagnetic signal and an acoustic signal, which electromagnetic signal and acoustic signal are received by respectively the base station electromagnetic receiver and acoustic receivers, whereby, on measuring difference in time-of-flight between the electromagnetic received signal and acoustic received signals, the bases station computes its own aforementioned third position and the aforementioned first position of each mobile unit. In an advantageous embodiment which allows positioning in relatively shorter periods of time without there being a positioning signal connection between the various individual units of the system, one or more of the systems base units and mobile units include inertial navigational means. Examples of inertial navigational means for this purpose are mechanical gyros, laser gyros of the fibre optical or ring laser type, multiaxial accelerometers and the like. The system may also be combined with other systems, such as, for example, satellite-based navigation systems, to extend its coverage area where such other systems are available.

Figure 8:
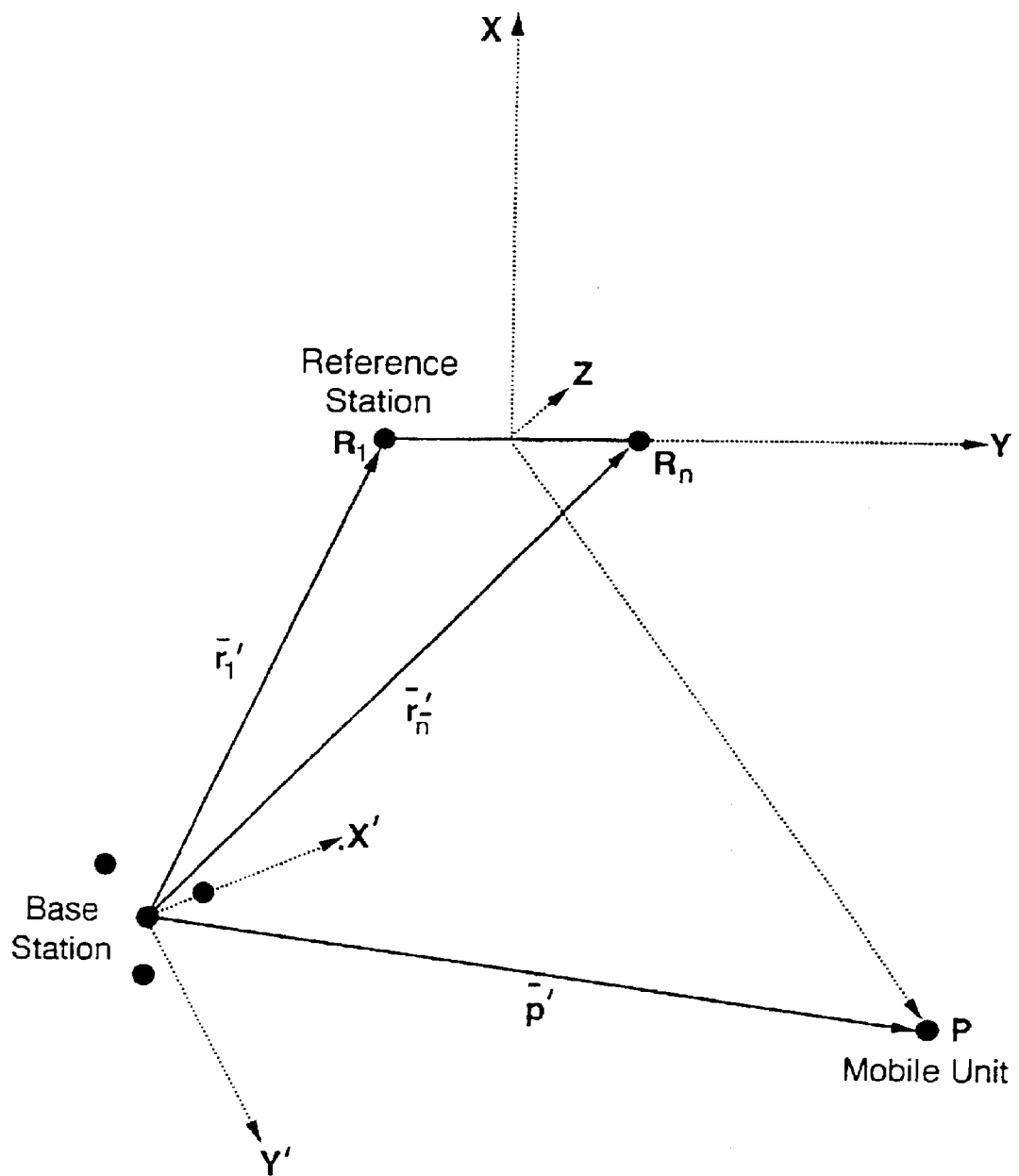
FIG. 8 shows schematically the geometrical parameters for position determination using the positioning system according to the invention.

FIG. 8 shows schematically the parameters which are included in the geometry of a system according to the invention for determining positions. The relative positions p', r0', and r1' are determined relative to the coordinate system X', Y' of the base station, and combined to give the position P relative to the coordinate system X, Y.

A positioning sequence can be initiated as required in, for example, a system configuration as shown in FIG. 2, by an operator pressing a button on a measuring sensor head on which is mounted a mobile positioning unit which is to be position-determined. When pressure is applied to the button. The mobile unit P transmits by means of its RF modem a call signal to a base station which in turn by means of its own RF modem sends a receipt signal back to the mobile unit P. As the operator makes a measurement using the measuring sensor head, the mobile unit P transmits via the RF modem a start message at the same time as it also transmits an acoustic signal. When the base station intercepts the RF signal, it initiates a collection of acoustic signals from its microphones. Having collected acoustic signals during a particular period of time, the base station computes the position of the mobile unit relative to its own. The base station then transmits via its RF modem a signal to the reference station characterised R0 which in its turn transmits an acoustic signal in response to the received RF signal, whereupon the base station collects these acoustic signals during a particular period of time and computes the position of the reference station R0 relative to its own. By combining these three relative positions the position of the mobile unit is then computed, and the position data is subsequently transmitted together with a time stamp via the RF modem to the mobile unit P which in turn relays the position data for storage and/or display together with other measuring data.

In an alternative embodiment for the use of the positioning system according to the invention in environments which are not suitable for the use of RF modems, optical modems which use the part of the electromagnetic spectrum which is in or close to the visible range will be used. Such optical modems will be suitable when using the positioning system in, for example, water, or in other environments where conditions may be unfavourable for radio waves owing to, for example, powerfull reflections, attenuation or radio frequency noise.

Besides transferring its own control data and position data, the positioning system according to the invention may also include transmission facilities and storage facilities for data relating to thickness distribution measurements according to the invention.

What is claimed is:

1. A method for measuring a material thickness distribution to be measured over a selected continuous area of an object, said method comprising the steps of:
    generating a broadband electric pulse excitation signal including frequency components within a current measuring range,
    converting the broadband electric pulse excitation signal to a broadband acoustic pulse excitation signal,
    sending the broadband acoustic pulse excitation signal towards the object,
    receiving an acoustic response signal emitted by the object as a response to the broadband acoustic pulse excitation signal,
    converting the acoustic response signal emitted from the object to an electric receive signal,
    conditioning the electric receive signal,
    processing the conditioned electric receive signal to derive the spectral distribution of the signal energy in the conditioned electric receive signal, and
    estimating the thickness distribution in the selected area of the object on the basis of the half wave resonance content of the signal energy spectral distribution of the conditioned electric receive signal, wherein the step of estimating includes the steps of:
        normalizing an energy spectrum on the total frequency characteristic of a transducer employed for converting the broadband electric pulse excitation signal to the broadband acoustic pulse excitation signal, and
        integrating the normalized energy spectrum over the selected continuous area of the object and a frequency range corresponding to the current thickness measurement range.

2. The method of claim 1, wherein the processing step includes the step of:
    identifying two main parts of the receive signal as being a reflection part and a tail part, respectively, and that parts of the spectral distribution of the signal energy of the conditioned electric receive signal which can be referred to as a respective main part are weighted differently from parts which can be referred to as a different respective main part when estimating the thickness distribution.

3. The method of claim 2, wherein the step of processing to derive the spectral distribution of the signal energy of the conditioned receive signal is carried out by means of a Fast Fourier Transform (FFT).

4. The method of claim 1, wherein the broadband electric pulse excitation signal is selected from the group of a sin(x)/c chirp, a transient signal, or a white noise signal.

5. The method of claim 4, wherein the duration of the broadband acoustic pulse excitation signal is adapted such that the broadband acoustic pulse excitation signal does not interfere with the acoustic response signal emitted by the object.

6. The method of claim 1, wherein the step of processing to derive the spectral distribution of the signal energy of the conditioned receive signal is carried out by means of a Fast Fourier Transform (FFT).

7. The method of claim 6, wherein the broadband electric pulse excitation signal is selected from the group of a sin(x)/c chirp, a transient signal, or a white noise signal.

8. The method of claim 2, wherein the broadband electric pulse excitation signal is selected from the group of a sin(x)/c chirp, a transient signal, or a white noise signal.

9. The method of claim 3, wherein the broadband electric pulse excitation signal is selected from the group of a sin(x)/c chirp, a transient signal, or a white noise signal.

10. The method of claim 1, wherein the duration of the broadband acoustic pulse excitation signal is adapted such that the broadband acoustic pulse excitation signal does not interfere with the acoustic response signal emitted by the object.

11. The method of claim 2, wherein the duration of the broadband acoustic pulse excitation signal is adapted such that the broadband acoustic pulse excitation signal does not interfere with the acoustic response signal emitted by the object.

12. The method of claim 3, wherein the duration of the broadband acoustic pulse excitation signal is adapted such that the broadband acoustic pulse excitation signal does not interfere with the acoustic response signal emitted by the object.

13. The method of claim 6, wherein the duration of the broadband acoustic pulse excitation signal is adapted such that the broadband acoustic pulse excitation signal does not interfere with the acoustic response signal emitted by the object.

14. The method of claim 5, wherein the processing step includes the step of:
    identifying two main parts of the receive signal as being a reflection part and a tail part, respectively, and that parts of the spectral distribution of the signal energy of the conditioned electric receive signal which can be referred to as a respective main part are weighted differently from parts which can be referred to as a different respective main part when estimating the thickness distribution.

15. The method of claim 5, wherein the step of processing to derive the spectral distribution of the signal energy of the conditioned receive signal is carried out by means of a Fast Fourier Transform (FFT).

16. The method of claim 12, wherein the broadband electric pulse excitation signal is selected from the group of a sin(x)/c chirp, a transient signal, or a white noise signal.

17. An apparatus for carrying out all-over measurement of a material thickness distribution in the material of an object to be measured over a selected continuous area of the object, comprising:
    a signal generator for generating a broadband, electric pulse excitation signal;
    a broadband sensor having at least one transducer for converting the broadband electric pulse excitation signal to a broadband acoustic pulse excitation signal, for sending the broadband acoustic pulse excitation signal towards the object, for receiving an acoustic response signal emitted by the object as a response to the broadband acoustic pulse excitation signal, and for converting the acoustic response signal emitted from the object to an electric receive signal;

a processing means for conditioning and spectrally analyzing the electric receive signal to derive the spectral distribution of the signal energy in the conditioned electric receive signal;

a calculating means for calculating an estimated thickness distribution in the selected area of the object on the basis of the spectral analysis results including the half wave resonance content of the signal energy spectral distribution of the conditioned electric receive signal, including:

means for normalizing an energy spectrum on the total frequency characteristic of a transducer employed for converting the broadband electric pulse excitation signal to the broadband acoustic pulse excitation signal, and means for integrating the normalized energy spectrum over the selected continuous area of the object and a frequency range corresponding to the current thickness measurement range; and a control means operatively connected to the signal generator, the broadband sensor, the processing means, and the calculating means for the control thereof.

18. The apparatus of claim 17, further comprising:

a registration means functionally connected to said control means and calculating means for registering the result of the thickness distribution computation.

19. The apparatus of claim 17, further comprising:

a data output device functionally connected to said control means and calculating means for processing and presentation of the computed thickness distribution.

* * * * *